United States Patent [19]
Kuizenga et al.

[11] Patent Number: 5,249,192
[45] Date of Patent: Sep. 28, 1993

[54] MULTIPLE FREQUENCY MEDICAL LASER

[75] Inventors: Dirk J. Kuizenga, Sunnyvale; Mark V. Ortiz, San Jose; Steven C. Murray, Menlo Park; Scott A. Davenport, Montara, all of Calif.

[73] Assignee: Laserscope, San Jose, Calif.

[21] Appl. No.: 722,493

[22] Filed: Jun. 27, 1991

[51] Int. Cl.⁵ .................................................. H01S 3/10
[52] U.S. Cl. ........................................ 372/23; 372/20; 372/99; 372/107; 372/108
[58] Field of Search ................................ 372/18–20, 372/23, 99, 107, 108, 98, 105

[56] References Cited

U.S. PATENT DOCUMENTS

| | | | |
|---|---|---|---|
| 3,626,322 | 12/1971 | Strouse | 372/19 |
| 4,783,787 | 11/1988 | Doi et al. | 372/19 |
| 4,823,351 | 4/1989 | Endemann et al. | 372/23 |
| 4,852,115 | 7/1989 | Viherkoski | 372/99 |
| 4,862,468 | 8/1989 | Fink | 372/23 |
| 4,920,541 | 4/1990 | Baumgartner et al. | 372/99 |
| 5,048,034 | 9/1991 | Tulip | 372/107 |
| 5,130,997 | 7/1992 | Ortiz et al. | 372/105 |

Primary Examiner—Léon Scott, Jr.
Attorney, Agent, or Firm—Fliesler, Dubb, Meyer and Lovejoy

[57] ABSTRACT

A laser system provides output wavelengths at near 1.06 and near 1.44 micron from an Nd:YAG gain medium, along with a frequency doubled output of the 1.06 micron line. This system is based on a laser resonator with a plurality of turning mirrors, each transmissive at a selective subset of the characteristic wavelengths of Nd:YAG and reflective at a selected output wavelength. The mechanism is coupled with the turning mirrors for selectively positioning one of the plurality of turning mirrors in the optical path, directing the beam on an output coupler having a fixed position with respect to a string of components for delivering the output beam to a surgical site. Also, the mechanism can selectively remove the turning mirror from the optical path. In this case, the beam is supplied to a frequency doubling alternate resonator design and output at the second harmonic of the 1.06 micron line is generated.

38 Claims, 8 Drawing Sheets

FIG.-15B ns which generate a plurality of output wavelengths, such as laser systems used in medical applications for supporting a variety of procedures requiring different wavelength laser beams. In particular, the present invention provides an Nd:YAG laser system providing outputs at near 1.44 micron, near 1.064 micron and near 0.532 micron at the second harmonic of 1.064 micron.

DESCRIPTION OF RELATED ART

Laser beams can be put to a variety of beneficial uses, which are wavelength specific. That is, to accomplish one goal, a laser providing an output at a first wavelength is required. To accomplish another goal, a laser providing an output at a second wavelength is required.

One such application of laser systems arises in the medical context. For instance, in some surgical procedures, an Nd:YAG laser is used at an output wavelength of 1.064 micron to achieve surgical or therapeutic results. Also, such laser system can be frequency-doubled to provide a 0.532 micron output beam to accomplish other surgical or therapeutic results.

It should be noted that the 0.532 micron light is strongly absorbed in blood and hence the 0.532 micron laser is very effective in cutting and vaporizing vascular tissue. The 1.064 micron light is not strongly absorbed in most tissue and penetrates deeply into tissue. With sufficient power at 1.064 micron (approximately 20 to 60 Watts) this causes sufficient heating of tissue to coagulate blood, and hence the 1.064 micron laser is effective in coagulation of bleeding during a surgical procedure.

It should also be noted that water has a strong absorption at 1.4 micron. Since all tissue has a large percentage of water, a laser at 1.4 micron is absorbed strongly in any tissue and hence a 1.4 micron laser is effective in cutting any tissue.

It is these properties of laser-tissue interaction that makes a combination 0.532 micron, 1.064 micron, and 1.44 micron laser very useful for surgical applications.

Because the 0.532 micron beam is the second harmonic of the 1.064 micron beam, both output wavelengths can be generated with a single laser system which includes a high-reflecting mirror, a pump cavity including the Nd:YAG rod, a turning mirror which can be positioned in and out of the beam path, and a second harmonic generation component set for generating the second harmonic output. In order to generate the 1.064 micron output, the turning mirror is placed in the optical path which directs the beam through an output coupler suited for the 1.064 micron line. For the frequency-doubled output, the turning mirror is moved out of the optical path and the oscillator lazes at 1.064 micron with a non-linear crystal and output coupler extracting the frequency-doubled output beam. A second harmonic generation mechanism which can be used in such a system is illustrated in U.S. Pat. No. 4,907,235 issued Mar. 6, 1990 entitled INTRA-CAVITY BEAM RELAY FOR OPTICAL HARMONIC GENERATION. Such patent is incorporated by reference for teaching the fundamentals of second harmonic generation.

Similarly, in our co-pending U.S. Patent application entitled, MEDICAL LASER APPARATUS, HIGH-POWERED RED LASER USED IN SAME, AND LASER RESONATOR WITH NON-LINEAR OUTPUT filed Dec. 18, 1990, Ser. No. 07/631,697 invented by Ortiz, et al. describes frequency doubling used to generate the 0.659 micron output from the 1.318 micron line of Nd:YAG. Such application is incorporated by reference as if fully set forth herein, which application is commonly owned by the same assignee as the present application and was so owned at the time of invention.

A problem arises when trying to use a single gain medium to provide gain at a plurality of the gain lines available in the gain medium. For instance, Nd:YAG is capable of oscillating at several wavelengths as described in Marling, "1.05–1.44 Micrometer Tunability and Performance of the CW $Nd^{3+}$ YAG LASER", *IEEE Journal of Quantum Electronics*, Vol. QE-14, No. 1, January, 1978. The Marling article is incorporated by reference as a teaching of the characteristic gain profile of Nd:YAG. To achieve outputs at selected gain lines in Nd:YAG, it is necessary to suppress the unwanted lines by introducing sufficient loss at these lines, particularly when trying to obtain an output at a low gain line such as 1.44 micron in the presence of the strong 1.064 line. As can be seen according to Marling, the output power of a 1.44 micron laser for a given input pump power in the tested system was 0.2% of the output power of a resonator designed for 1.064 micron output. (Id., Table 1 at page 61) Thus, it is apparent that the gain of the 1.44 line is much less than the gain of the 1.064 line. In an oscillator which is designed for the 1.44 line, the 1.064 line must be significantly suppressed. Even a small amount of reflectivity of the components in the resonator at the 1.064 wavelength will result in domination of the 1.064 wavelength and inability to generate a 1.44 micron output.

According to Marling, in order to achieve a 1.44 micron output, a specially coated reflectors and a tuned solid etalon had to be placed in the cavity to suppress the higher gain lines of Nd:YAG, including the 1.064 line and the lines in the 1.32–1.36 micron range. In the Marling configuration, only very low power at the 1.44 line was achieved.

To achieve a laser system which is capable of selectively providing an output of either 1.064 and 1.44 micron therefore presents significant design problems. Such a system is described in U.K. patent application, Publication No. GB2197748A, published on 25 May 1988 claiming priority to U.S. application Ser. No. 933,103 filed 20 Nov. 1986, entitled LONG WAVELENGTH Nd:YAG LASER invented by Tulip. As can be seen in the Tulip application, to change the output beam from 1.064 to 1.44 micron, both laser mirrors have to be changed out using a mechanism which moves the output coupler and high-reflecting mirrors for the 1.064 line out of the beam path, and replaces them by a high-reflector and output coupler designed for the 1.44 line. These two reflectors for 1.44 micron are both high transmitting at 1.064 micron, and this means that to suppress the high gain 1.064 micron line takes at least the low reflection off two mirror surfaces. (We have also found that having just one high transmitting mirror at 1.064 micron is generally not sufficient to suppress the 1.064 micron oscillations.) This mechanism to switch both mirrors presents significant problems in maintaining constant alignment of the output beam as the output coupling mirror is changed and is also mechanically quite complicated. If applied as suggested by Tulip to surgical applications which require coupling of the output beam into a fiberoptic delivery system, the alignment of the two resonators which are moved into and out of the beam path would be critical, making it difficult to ensure efficient coupling into the fiber.

Tulip also suggests without implementation details that the high gain line at 1.06 micron could be suppressed by a silicon window one centimeter thick placed in the beam path, which will absorb the 1.06 micron wavelength. Such silicon could be used to select between the 1.44 micron and 1.064 micron lines in Nd:YAG. However, it is believed that the absorbing silicon is not perfectly transparent at 1.44 micron and will cost significant gain in the resonator at that already low gain line. Further, the absorbing window technique is not readily extended to other wavelengths, because of the difficulty in identifying and obtaining absorbing window materials for a given wavelength.

Tulip also suggests without enabling details that other wavelength selecting means such as prisms and defraction gratings could be used in such systems. However, all of the alternatives suggested by Tulip are mechanically quite complex, are not suitable for randomly polarized beams, or cost gain in the laser resonator.

As explained in the Tulip application, it is desirable to provide a laser system which provides output at 1.44 micron and 1.06 micron for surgical applications. The 1.44 micron line is excellent for cutting most kinds of tissue due to water absorption as described previously, while the 1.06 micron line is used for causing coagulation. It is also desirable to be able to provide a second harmonic of at least the 1.06 micron line for other surgical uses. In the prior art, it has been impractical to provide such multiple wavelength systems.

SUMMARY OF THE INVENTION

The present invention provides a laser system capable of producing an output at a plurality of wavelengths. The laser system includes a high-reflector and a fixed output coupler in a resonant path, each having characteristic reflectivities designed for the plurality of wavelengths. A gain medium is mounted in the resonant path for providing laser gain at the plurality of wavelengths. A mechanism for selectively suppressing gain at subsets of the plurality of wavelengths to enable gain at a selected wavelength is provided in the resonator. The mechanism includes a plurality of non-absorbing, wavelength-selective elements and a mechanism for positioning one of the wavelength-selective elements in the resonant path to enable gain at a selected wavelength. For randomly polarized laser systems, the wavelength-selective element should be polarization insensitive.

According to one aspect of the invention, the wavelength-selective elements are turning mirrors, or other polarization insensitive elements, which can be selectively positioned in the beam path. The turning mirrors are coated so as to be reflective at a selected wavelength and transmissive at other higher gain wavelengths in the plurality.

According to another aspect of the invention, the positioning means can selectively position one of the turning mirrors or none of the turning mirrors in the beam path to generate selected outputs through the fixed output coupler. When no turning mirror is in the beam path, an alternative resonator is formed to extract output beams having other selected characteristics, such as by frequency doubling one of the subset of output lines. Thus, the alternative resonator may include a Q-switch, a non-linear crystal and an output coupler which is highly reflective at one of the characteristic wavelengths of the gain medium while transmissive at the desired wavelength derived from the non-linear crystal.

According to yet another aspect of the present invention, the gain medium is Nd:YAG and the plurality of wavelengths includes a wavelength near 1.06 micron and a wavelength near 1.44 micron. In this embodiment, one of the turning mirrors will be transmissive at 1.06 micron and highly reflective at 1.44 micron, while another of the turning mirrors is highly reflective at 1.06 micron.

It should be noted that in the resonator with a single turning mirror, that as light travels once around the resonator, it reflects once off each end mirror, but reflects twice off the turning mirror. This means that a single turning mirror with high transmission at 1.064 micron provides just as much suppression as the two mirror resonator proposed previously by Tulip, but with the turning mirror approach, we obtain this suppression without moving the output coupler and hence we obtain much better alignment into any devices outside the resonator. The alternative resonator includes means for extracting a second harmonic of the 1.06 line.

It is found as well that the laser system taught by the present invention provides an excellent configuration for producing any desired low gain line, such as the 1.44 line in Nd:YAG, with or without the multiple wavelength options.

In the laser system which provides outputs in at least two characteristic wavelengths of the gain medium and also provides alternative resonator capability, such as second harmonic generation, the selectable tuning mirrors are aligned in the beam path at an angle of incidence in the optical path near 45°. This enables compact layout of the laser system including the beam delivery system for the plurality of output modes. Other configurations with the angle of incidence less than 45° on the turning mirror are also possible. It is possible to make a 45° high reflector at 1.44 micron that is polarization insensitive, but in general the smaller the angle of incidence, the easier it is to make polarization insensitive mirror for the high reflector, and simultaneously obtain high reflection for the wavelengths that have to be suppressed.

The present invention is particularly suited for a laser system which generates outputs at both 1.06 and 1.44 micron, together with the ability to provide a frequency-doubled output of the 1.06 micron line. As mentioned above, these wavelengths are particularly suited to medical applications. Such a system will have a wide variety of surgical applications that may reduce the need for large numbers of laser systems in operating rooms. This provides greater access to laser medical procedures in a wider variety of places.

Other aspects and advantages of the present invention can be seen upon review of the figures, the detailed description and the claims which follow.

DETAILED DESCRIPTION

A detailed description of the preferred embodiments of the present invention is provided with reference to the Figures.

Figure 1:
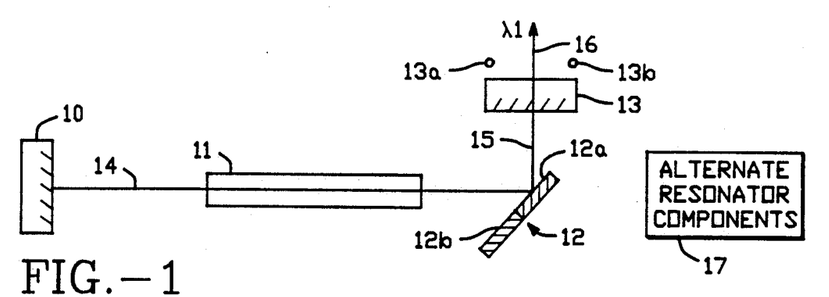
FIGS. 1-3 illustrate the laser system according to the present invention with the wavelength-selective elements in respective positions to achieve a desired output beam.
Figure 2:
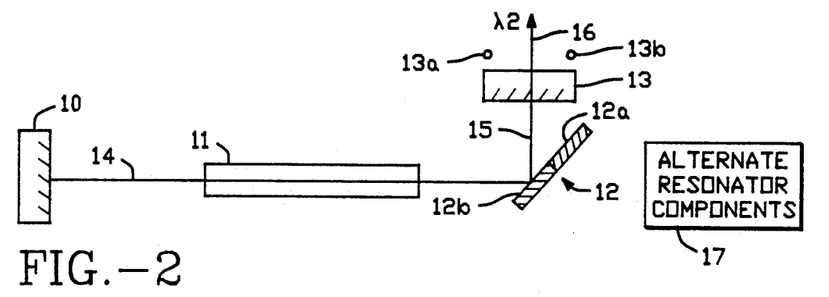
Figure 3:
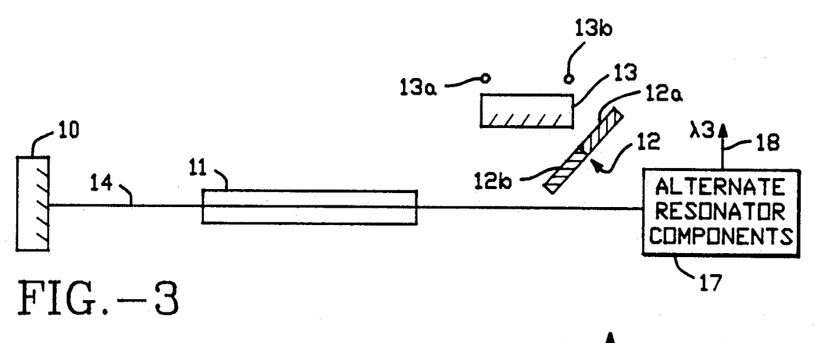

FIGS. 1-3 illustrate three states of a laser system according to one embodiment of the present invention. The laser system includes a high-reflecting mirror 10, a gain medium 11, a wavelength-selective turning mirror assembly 12, and an output coupler 13 mounted in a fixed position that is adjustable as indicated schematically by adjustment nobs 13a, 13b. The fixed output coupler 13 is critical for coupling the output beams into external beam delivery systems, as described below.

The output coupler 13 and high-reflecting mirror 10 define a laser resonator for a plurality of wavelengths. The gain medium 11 characterized by providing laser gain at a number of characteristic wavelengths. The plurality of wavelengths for which the laser resonator is designed is at least a subset of the characteristic wavelengths of the gain medium 11.

The wavelength-selective turning mirror assembly 12 includes a plurality of turning mirrors, or other beam directing elements, and a mechanism (described in more detail below) for positioning a selected one of the turning mirrors in the beam path. In the preferred system with a non-polarized cavity mode, such as generated by Nd:YAG media, the beam directing element must be polarization insensitive. This is because at the pump power into the Nd:YAG to get sufficient output power, there are significant thermal gradients in the YAG rod that cause thermal focusing and depolarization of the beam. These YAG lasers want to oscillate unpolarized, and any polarizing elements in the resonator significantly reduce the output power.

The resonator formed by the high-reflecting mirror 10 and the output coupler 13 includes optical path 14 which passes through the gain medium 11 and intersects the turning mirror assembly 12 in the optical path at an angle of incidence, in the preferred embodiment, of 45° or less. This results in turning the resonant path by 90° or less, which resonant path includes the optical path 14 and the output leg 15.

In the preferred system, the gain medium 11 comprises Nd:YAG pumped by an arc lamp assembly. Obviously, a variety of other pumping mechanisms and gain media are available and will be appreciated by those skilled in the art. Each gain medium has a plurality of characteristic wavelengths which it can provide significant laser gain. For Nd:YAG, these wavelengths are described in detail in the Marling reference referred to and incorporated by reference above. The high-reflecting mirror 10 and output coupler 13 are coated so that a subset of the characteristic wavelengths of the gain medium can laze along the resonant path. For instance, in a preferred system, the Nd:YAG gain medium produces an output along path 16 at a wavelength near 1.06 micron or a wavelength near 1.44 micron. In this embodiment, the output coupler is coated so as to be significantly reflective and provide optimum output coupling at near 1.06 micron and at near 1.44 micron. Typical reflections could be 70-80% at 1.06 and 90-95% at 1.44 micron. The high-reflecting mirror 10 is coated so as to be highly reflective at both wavelengths near 1.06 micron and near 1.44 micron.

The turning mirror assembly 12 includes a first reflector 12a and a second reflector 12b. The first reflector 12a is highly reflective at near 1.06 micron. The second reflector 12b is highly reflective at near 1.44 micron and significantly transmissive (e.g., 80% or sufficient to suppress oscillation) at near 1.06 micron.

Thus, as illustrated in FIG. 1, when the turning mirror assembly 12 is positioned so that reflector 12a is in the optical path 14, an output at wavelength λ1, equal to near 1.06 micron in the preferred system, is generated. As illustrated in FIG. 2, when the turning mirror assembly 12 is positioned so that reflector 12b is in the optical path 14, then an output at λ2 is generated, at or near 1.44 micron in the preferred system.

The system generating outputs at near 1.06 micron and near 1.44 micron is particularly illustrative of the capabilities of the present invention in providing both low gain and high gain outputs through a fixed output coupler to beam delivery systems, from a single gain medium. In particular, the gain in Nd:YAG at 1.06 micron is much greater than the gain at 1.44 micron.

When the turning mirror assembly 12 is positioned such that reflector 12a is in the beam path, the laser will oscillate at the high gain line, to the exclusion of the lower gain line. Other elements for suppression of the lower gain line are not required when the difference in gain is large, as in the case of the 1.06 and 1.44 lines of Nd:YAG.

As illustrated in FIG. 2 however, when it is desired to generate an output of near 1.44 micron, active suppression of the much higher gain 1.06 line and other high gain lines in Nd:YAG is required. Suppression of the line near 1.06 micron is achieved by making the reflector 12b transmissive at the 1.06 micron line. The turning mirror 12b diverts the 1.06 micron light from the resonant path for a reflection in each direction, causing two reflections per roundtrip in the resonator, and giving enough loss at the 1.06 micron line to prevent lasing at the 1.06 micron line, and to enable lasing at the 1.44 micron line.

The other high gain lines on the Nd:YAG are suppressed using the high-reflector 10 and the output coupler 13. For instance, such optics are coated so that they are transmissive at wavelengths near 1.32 micron. The turning mirror 12b can also be designed to suppress the wavelengths near 1.32 micron.

As illustrated in FIG. 3, the turning mirror assembly 12 can be positioned so that neither reflector 12a nor reflector 12b lie in the optical path 14. In this state, the beam enters alternate resonator components 17. The alternate resonator components 17 then form a laser resonator with the high-reflecting mirror 10 which generates an output beam λ3 along path 18.

The alternate resonator components 17 may be composed, for instance, of mechanism including an intracavity, or outside cavity, non-linear crystal for extracting harmonic or sum-of-frequency beams from one of the characteristic wavelengths of the gain medium 11. A wide variety of alternate resonator components 17 could be placed in the optical path 14 for use in this third state of the laser system, such as a Q-switch, polarizers, amplifiers, testing or measuring equipment, other wavelength-selective elements such as prisms or defraction gratings, or other components which would be adapted to a specific application of the laser system. As described in detail below, the alternate resonator components 17 in the preferred system comprise the means for extracting the second harmonic of wavelengths near 1.06 micron so that the available outputs in the preferred system include λ1 near 1.06 micron, λ2 near 1.44 micron, and λ3 near 0.53 micron.

The turning mirror assembly according to the preferred embodiment is placed in the optical path 14 at an angle of incidence near 45°, to allow compact layout of laser systems. However, in some systems where it is necessary to suppress gain at wavelengths that are more closely spaced than at 1.44 micron and 1.06 micron, it may be necessary or desirable to place the turning mirror assembly at much smaller angles of incidence, to accommodate the optics design. Because the smaller angles of incidence result in less turning of the output leg 15, it may be necessary to space the components of the resonator further apart to achieve sufficient divergence of the beam paths. As mentioned previously, for smaller angles it is easier to get non-polarizing reflectors and it is also easier to get suppression of unwanted lines.

Figure 4:
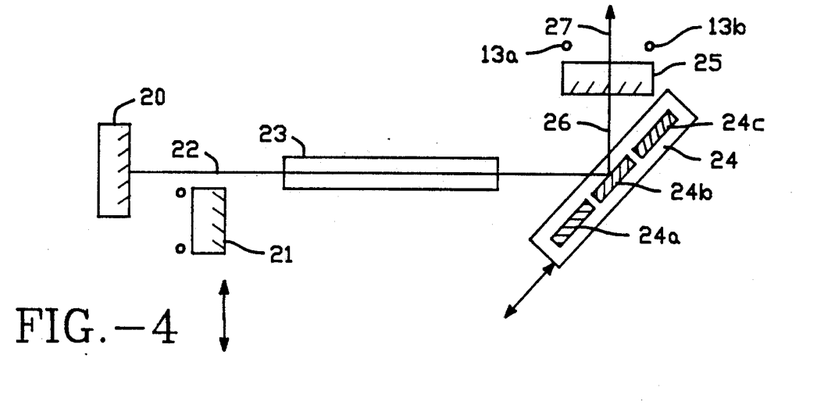
FIG. 4 illustrates an alternative embodiment of the laser system of FIGS 1-3.

As illustrated in FIG. 4, an alternate embodiment of the present invention is provided. In this embodiment, there is a first high-reflecting mirror 20 and a second high-reflecting mirror 21. The high-reflecting mirror 21 may be positioned in or out of optical path 22. Gain medium 23 is provided along the optical path 22. A turning mirror mechanism 24 is mounted along the optical path 22 and a fixed output coupler 25 is mounted in the output leg 26 of the resonant path. The turning mirror mechanism 24 includes a first turning reflector 24a, a second turning reflector 24b, and a third turning reflector 24c. The output coupler 25 is adapted for resonating at at least three wavelengths which are selected by the turning mirror assembly 24. The high-reflector 20 is adapted for high-reflection at the higher gain line or lines of the gain medium 23 while the high-reflector 21 is highly reflective at the lower gain line or lines of the gain medium 23. This mechanism will allow greater suppression of high gain lines of the gain medium, and possibly much greater wavelength selectability of the resonator, by providing an alternative high-reflector 21. However, the system maintains a fixed output coupler 25 which facilitates the coupling of the output beam 27 into external beam line optics such as fiberoptic delivery systems and the like.

Note that FIGS. 1–4 illustrate two possible embodiments of the turning mirror. In FIGS. 1–3, a single substrate 12 is shown with two reflectors on this substrate. This makes alignment of the two resonators easier as the turning mirror mechanism switches between the two mirrors, but the fabrication of this optic is more difficult. Alternatively, FIG. 4 shows two or more separate mirrors, but these mirrors then have to be precisely aligned in the mirror assembly 24.

Figure 5:
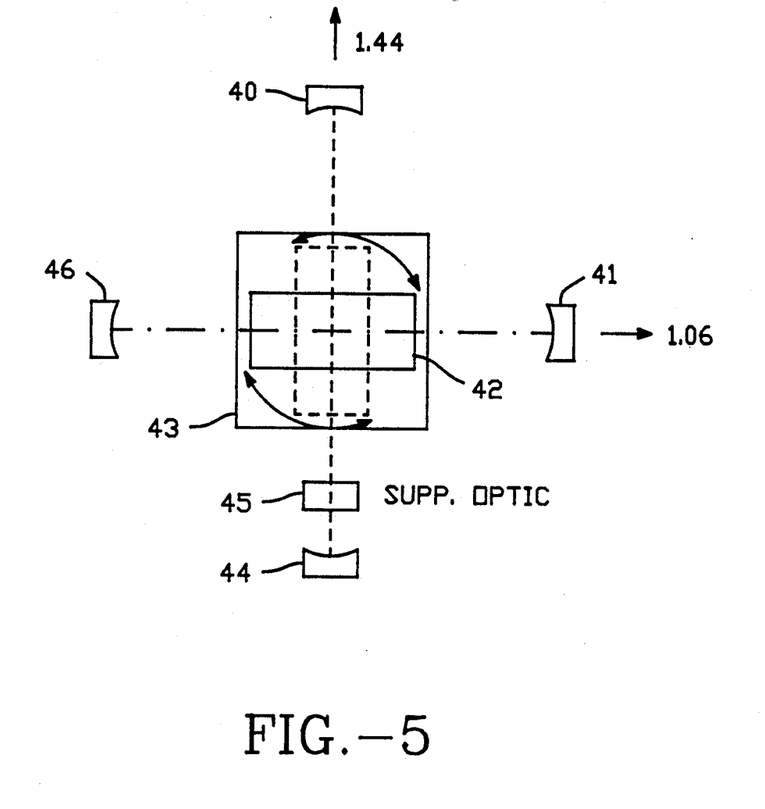
FIG. 5 illustrates an alternative system for obtaining a plurality of output lines with fixed output couplers according to the present invention.

FIG. 5 illustrates an alternative embodiment for achieving the aspect of the invention which calls for fixed output couplers feeding beam delivery systems. In the embodiment illustrated in FIG. 5, the laser system is composed of two fixed output couplers 40, 41, and a gain medium 42 mounted on a carriage 43. The gain medium 42, such as a pump cavity containing an Nd:YAG rod, is rotatable on the carriage 43 to align with the first output coupler 40 or the second output coupler 41, depending on the output wavelength desired. Thus, for an Nd:YAG system generating both the 1.44 and 1.06 micron lines, the output coupler 40 would be transmissive at the high gain lines and about 80% reflective at the 1.44 line. Opposite the output coupler 40, a high-reflecting mirror 44 would be mounted, which is transmissive at the high gain lines in the gain medium but reflective at the 1.44 gain line. In addition, there may be a suppression optic 45 mounted in the resonant path for the 1.44 line if necessary. Such suppression optic could be an etalon, or a silicon window as suggested by Tulip in the U.K. patent application, Publication No. GB2197748A referred to above.

For the generating output at the 1.06 micron lines, a high-reflector 46 is mounted in alignment with the output coupler 41.

Thus, the gain medium 42 has a first position aligned with the 1.06 micron resonant cavity, and a second position indicated by dotted lines rotated from the first position as indicated by the arrows, in which the gain medium is aligned with the resonant cavity for the 1.44 micron line.

The alignment of the gain medium 42 with the respective resonant cavities in the laser system of FIG. 5 is much less critical than the alignment of the output couplers with beam delivery systems, particularly in randomly polarized systems.

The concept shown in FIG. 5 can obviously be extended to a plurality of wavelengths by adding more mirror pairs.

Figure 6:
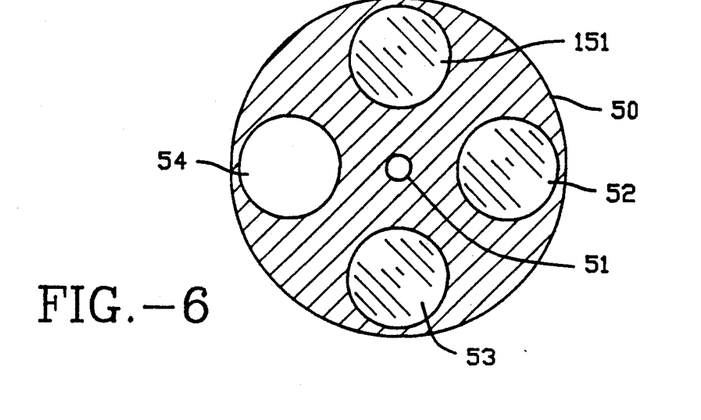
FIG. 6 illustrates one embodiment for positioning wavelength-selective elements in the beam path.
Figure 7:
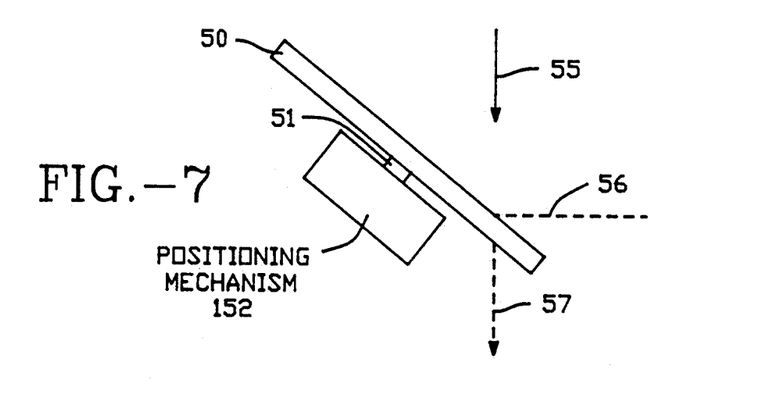
FIG. 7 illustrates a mechanism for positioning the wavelength-selective elements of FIG. 6.

FIGS. 6–9 illustrate possible designs for the turning mirror assemblies according to the present invention. FIGS. 6 and 7 illustrate a wheel 50 having an axis 51 which is positioned by a positioning mechanism 52 such as a stepper motor or other mechanism for rotating the wheel 50 with stops for each of a plurality of turning mirrors. As can be seen, the wheel 50 includes a first turning mirror 51, a second turning mirror 52, and a third turning mirror 53. In the fourth position, a Passage 54 is made in the wheel which is transmissive at all of the wavelengths of interest. Thus, by rotating the wheel, the desired turning mirror can be placed in the beam path while maintaining precise alignment of the turning mirror. As illustrated in FIG. 7, the beam path for a 45° angle of incidence would strike the wheel 50 along line 55, and reflect along line 56 for eachof the turning mirrors 51, 52 and 53. When the passage 54 is aligned with the beam path 55, the beam traverses through the turning mirror mechanism along line 57.

Figures 8, 9:
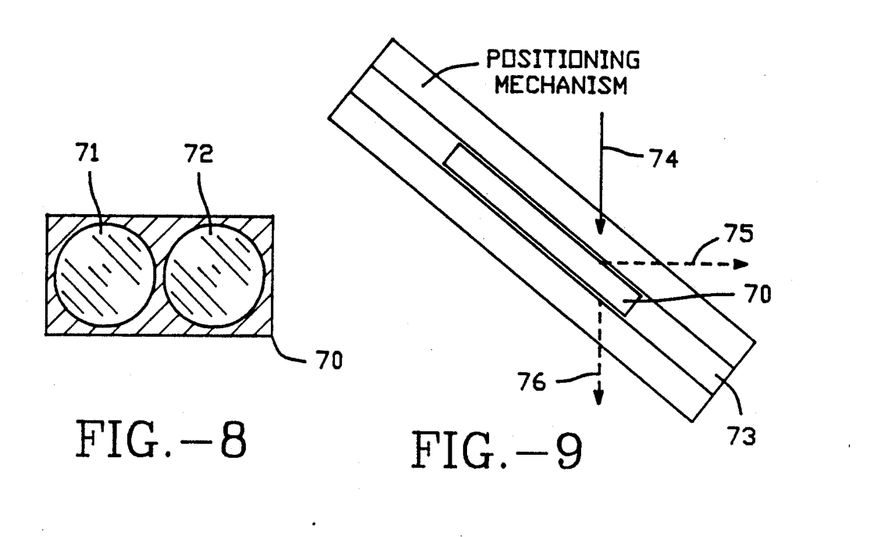
FIG. 8 illustrates another embodiment for positioning wavelength-selective elements in the beam path.
FIG. 9 illustrates a mechanism for positioning the wavelength-selective elements of FIG. 8.

FIGS. 8 and 9 illustrate an alternative turning mirror mechanism. As illustrated in FIG. 8, a bracket 70 holds a plurality of turning mirrors 71 and 72. The bracket 70 is mounted on a rail 73 shown in FIG. 9, which allows positioning of the bracket 70 so that an incoming beam along line 74 strikes a turning mirror and reflects along line 75 or misses the bracket 70 altogether and continues traveling along line 76.

Alternative systems could coat a single substrate (such as shown in FIGS. 1-3) with a plurality of reflectors, and position the substrate so that the selected reflector lies in the beam path.

As will be apparent to those skilled in the art, FIGS. 6-9 are representative of many equivalent techniques for positioning turning mirrors in the laser system of the present invention.

As will be appreciated by those skilled in the art, other wavelength-selective elements could be used to achieve wavelength selection in systems according to the present invention. For instance, the turning mirrors could be replaced by prism mechanisms and the like, in systems operating with polarized cavity modes, such as those using Nd:YLF gain media. The preferred system, however, utilizes polarization insensitive beam-directing elements, such as turning mirrors.

FIGS. 10-15 provide a detailed implementation of a preferred laser system according to the present invention. This laser system is used for medical applications and provides output beams at 1.06 micron and 1.44 micron, and a frequency-doubled output at 532 micron for use in surgical applications.

Figure 10:
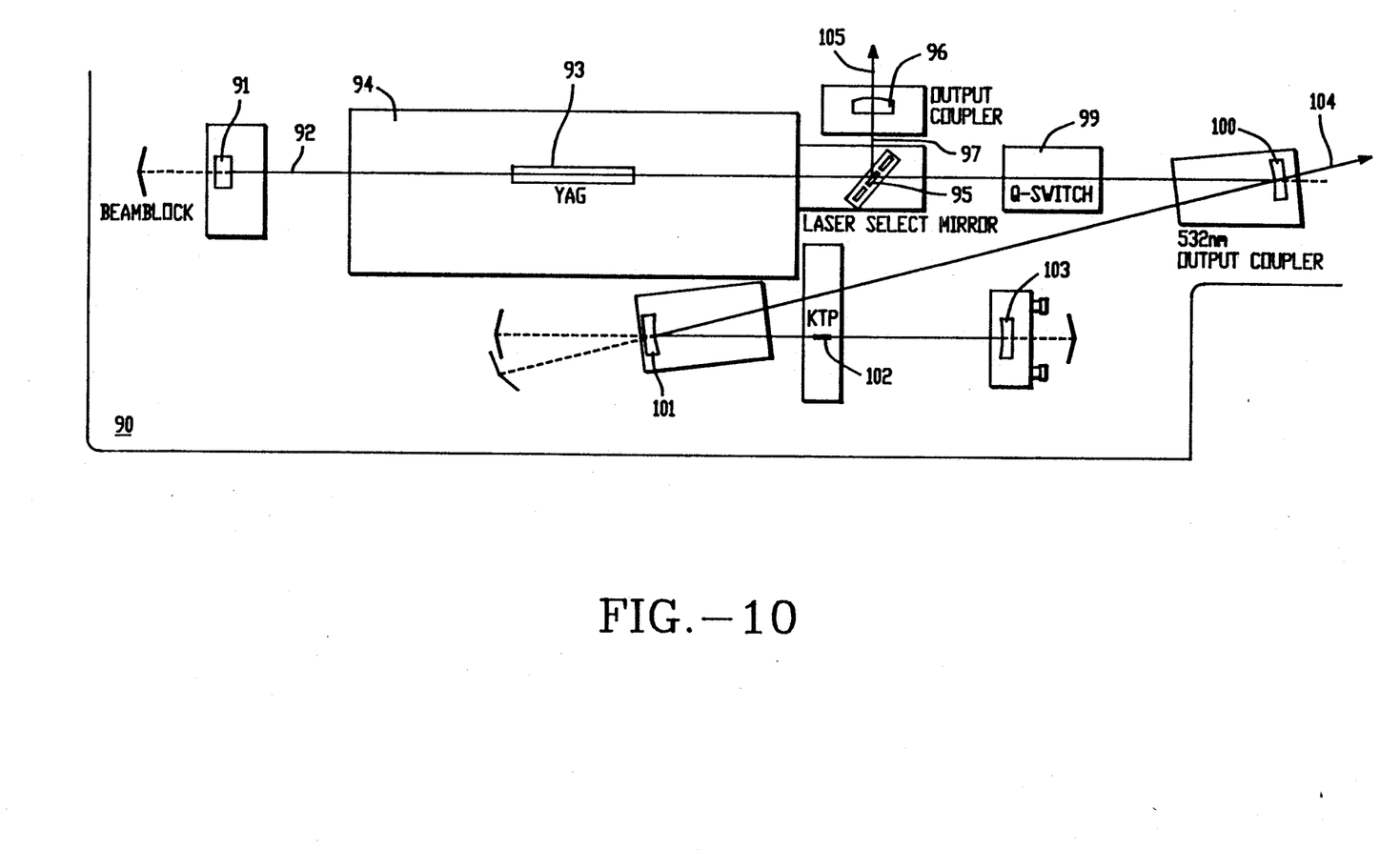
FIG. 10 illustrates the laser system according to the present invention.
Figure 11A:
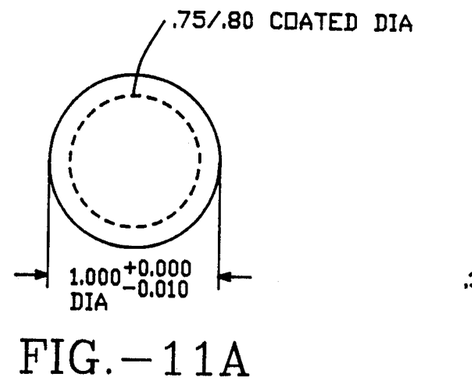
FIGS. 11A, and 11B illustrate the high-reflecting mirror of the resonator of FIG. 10.
Figure 11B:
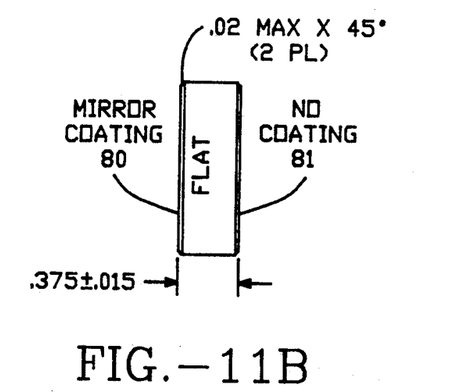

The resonator is mounted on a plate 90. A high-reflecting back mirror 91 having optics as illustrated with respect to FIGS. 11A and 11B is mounted in the optical path 92. A gain medium of Nd:YAG 93 in a pump cavity 94, which includes a krypton arc lamp, is also mounted in the beam path 92. For at least the 1.44 micron mode, the pump energy is pulsed to achieve greater efficiency. The YAG rod in the preferred system is about 79 mm long and from 4 to 6.35 mm in diameter, with anti-reflective coatings providing less than 0.25% reflection at 1.064 and 1.44 micron.

A pump energy source is provided by the arc lamp within the pump cavity 94. The pump energy source is controlled using a system such as that described in co-pending U.S. patent application entitled FREQUENCY DOUBLED SOLID STATE LASER HAVING PROGRAMMABLE PUMP POWER MODES AND METHOD FOR CONTROLLING LASERS, Ser. No. 07/689,356, Filed Apr. 22, 1991, which is incorporated by reference as if fully set forth herein.

Figure 12A:
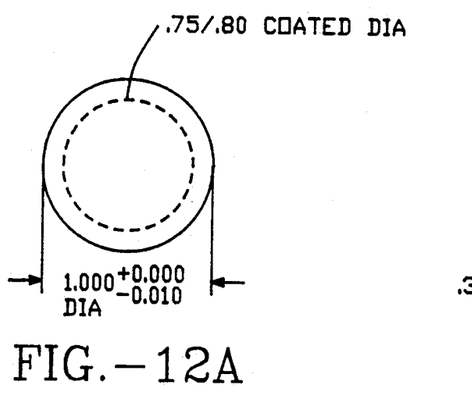
FIGS. 12A and 12B illustrate the output coupler for the 1.06 and 1.44 output beams in the resonator of FIG. 10.
Figure 12B:
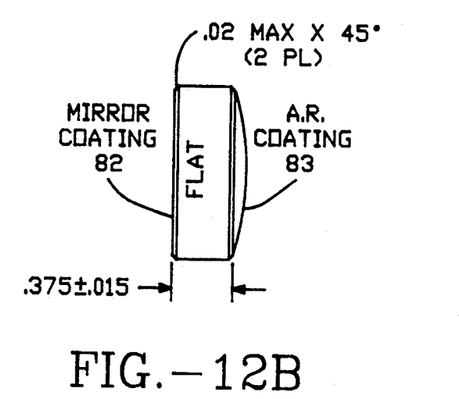

A laser output select mirror mechanism 95 lies along the beam path 92 adjacent to the pump cavity 94. An output coupler 96 having optics as illustrated with respect to FIGS. 12A and 12B is mounted along an output leg 97, which defines a resonant path between the high-reflector 91 and the output coupler 96. The 1.064 micron and 1.44 micron lines are generated along the same path 105.

Continuing along the beam path 92 are alternate resonator components including a Q-switch 99, a turning mirror 100 which is coated to provide output coupling at 0.532 micron, a turning mirror 101, a non-linear crystal 102, which is KTP in the preferred system, and a back mirror 103. The back mirror 103 and turning mirrors 100, 101 are highly reflective at the 1.06 micron line. Mirrors 101 and 103 are also highly reflective at the 0.532 micron line, while the output coupler turning mirror 100 is transmissive at the 0.532 micron line. Turning mirrors 100 and 101 have radius of curvature of 50 and 20 cm, respectively, to provide an optical relay with magnification 2.5 between the YAG rod output and the KTP crystal. This alternate resonator provides an output beam along path 104, when the laser select mirror 95 is positioned to allow lasing through the alternate resonator components.

The second harmonic generation components beginning with the Q-switch 99 through the back mirror 103 are designed as described in U.S. Pat. No. 4,907,235, referred to and incorporated by reference above. Also, similar system for generating frequency doubling at the 1.32 micron line provide a 0.659 micron output is illustrated in our co-pending U.S. patent application Ser. No. 07/631,697, referred to and incorporated by reference above.

Figure 15A:
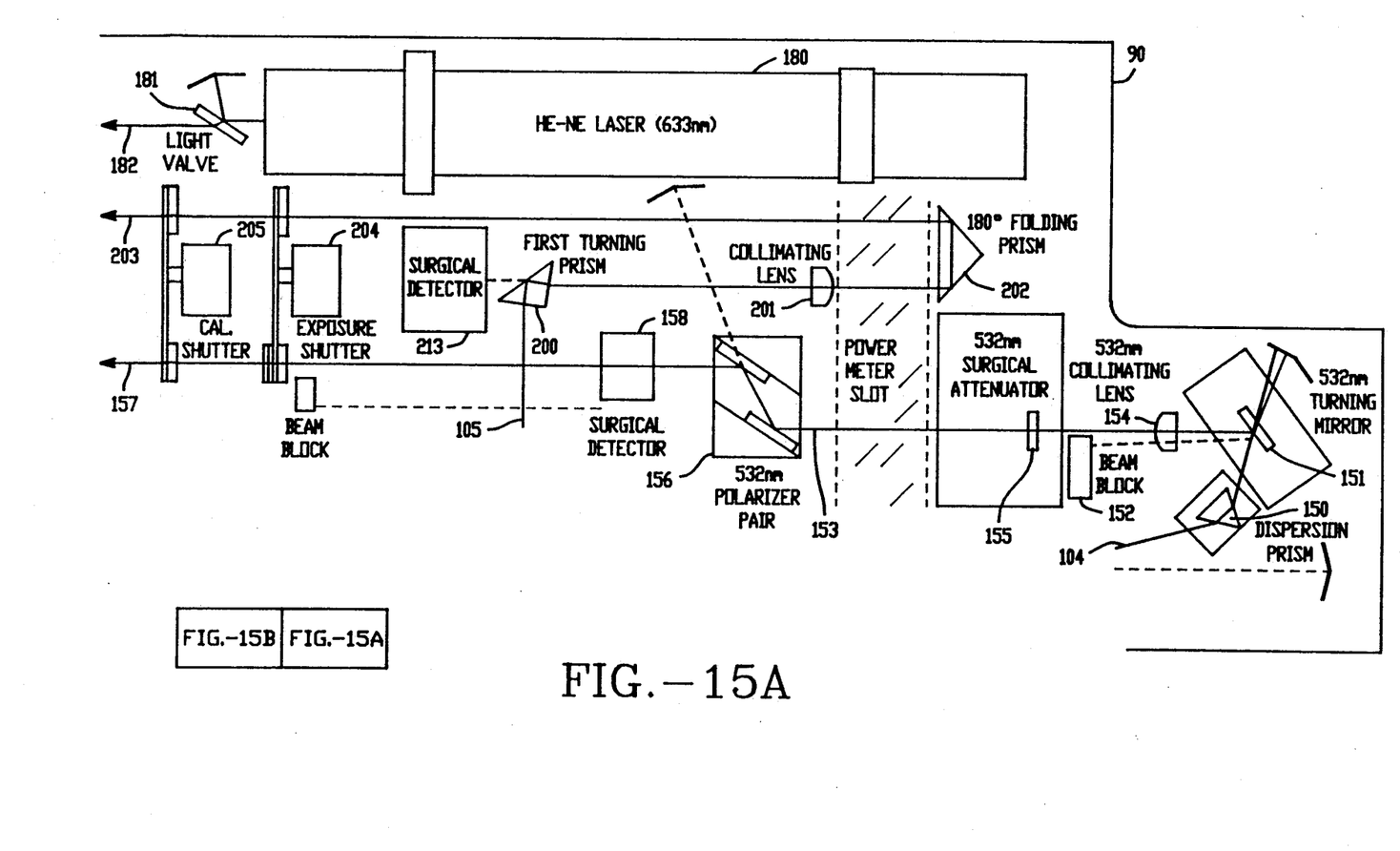
FIGS 15A and B illustrates the components in the beam path external to the laser resonator for the surgical application according to a preferred embodiment of the present invention.
Figure 15B:
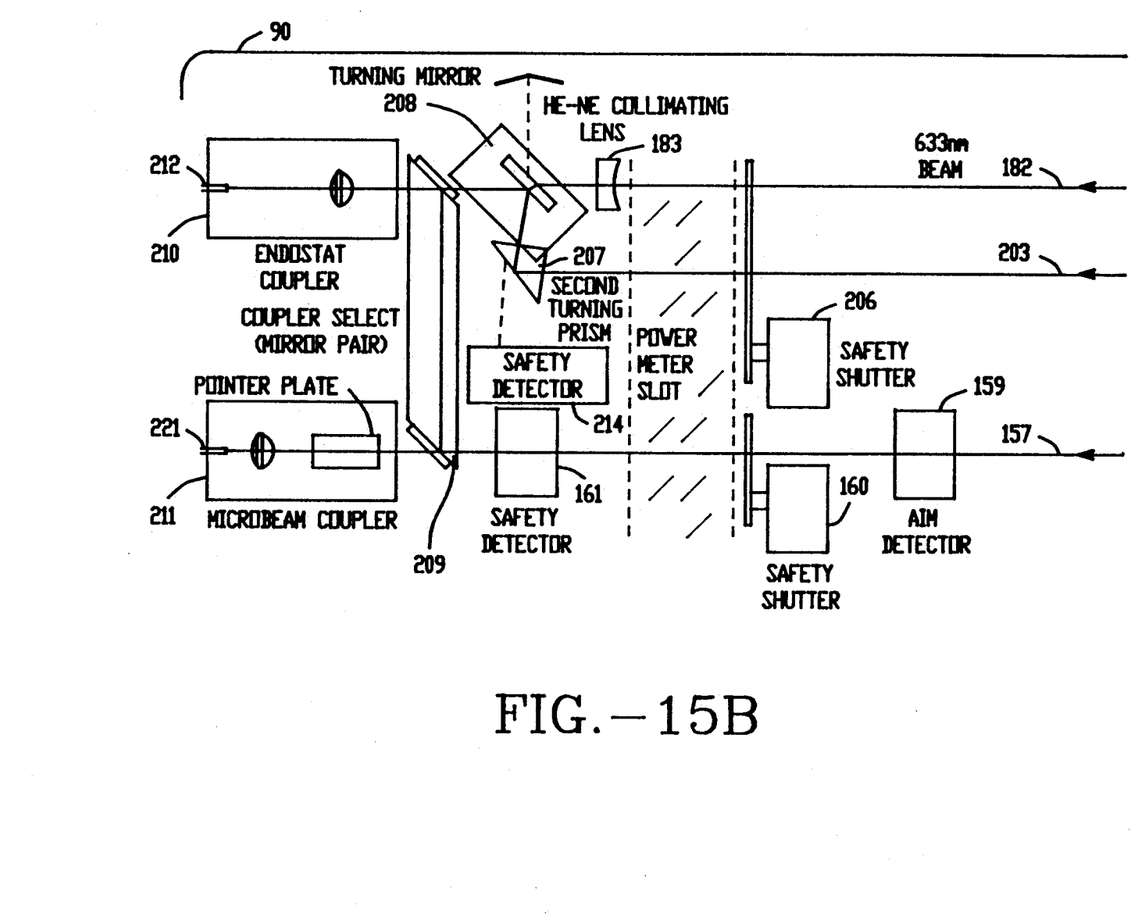

The beams along paths 105 and 104 are supplied into beam line components illustrated in FIG. 15 and onto a fiberoptic delivery system coupled to an endostat and/or microbeam couplers for use in surgical applications.

The optics for the high-reflector 91, the turning mirrors in the laser select mechanism 95, and the output coupler 96 are described with reference to FIGS. 11A, 11B, 12A, 12B, 13A and 13B. These optics are manufactured by commercial vendors of laser optics such as Spectra Physics Optics Corporation, 1330 W. Middlefield Road, Mountain View, Calif., and are obtained through custom orders by Applicant. As shown in FIGS. 11A and 11B, the high-reflecting mirror 91 is manufactured on a 1-inch diameter by 0.375 inch thick BK7 or fused silica substrate. It is coated on the inside 80 so that it is reflective at greater than 99.8% at both 1.064 micron and 1.440 micron for a 0° angle of incidence. It is less than 50% reflective at 1.320 micron at 0° angle of incidence. The back surface 81 is flat and uncoated.

The output coupler is illustrated in FIGS. 12A and 12B. It is formed on a 1-inch diameter Infrasil 301 substrate which is 0.375 inches thick, exclusive of the curved output side. This output coupler is coated on the inside 82 so that it is reflective at 88.0±2% at 1.064 micron and at 90.0±2% at 1.440 micron for a 0° angle of incidence, and reflective at 50% at 1.320 micron at a 0° angle of incidence. On the output side 83, an anti-reflective coating which is less than 0.25% reflective at 1.064 micron and less than 0.25% reflective at 1.440 micron at a 0° angle of incidence. The output surface is convex. This outside curved surface acts as a lens to aid in coupling the laser output to the fiber. The curvature of this surface is designed together with the other optics in the external beamline to match the beam into a fiber, but the actual curvature is not relevant to the actual operation of the laser.

Figure 13A:
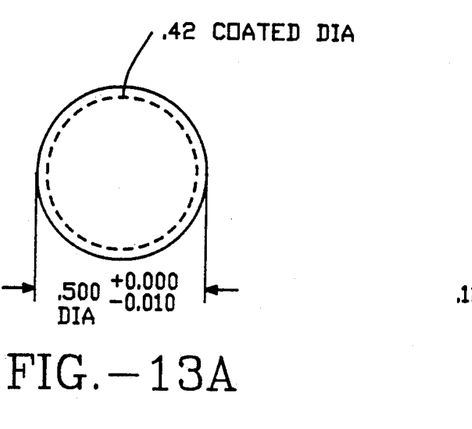
FIGS. 13A and 13B illustrate the turning mirrors used in the resonator of FIG. 10.
Figure 13B:
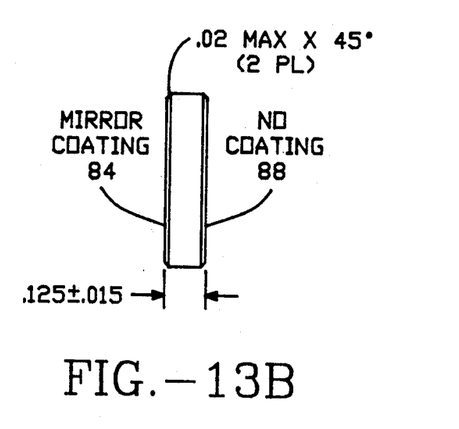

The turning mirrors in the preferred system are formed on separate, identical substrates. The substrate is illustrated in FIGS. 13A and 13B. As can be seen, the substrate is a 0.500 inch diameter by 0.125 inch thick disc, manufactured of BK-7 or fused silica. The mirror coating on surface 84 as illustrated in FIG. 13B for first mode is reflective at ≧99.8% at 1.064 micron with random polarization at 45° angle of incidence. There is no coatin on the back side 85.

The second turning mirror for the 1.44 micron output mode has a mirror coating 84 that is ≧99.8% reflective at 1.440 micron with random polarization at a 45° angle of incidence. The coating also has a less than 20% reflectivity at 1.064 micron for "S" and "P" polarization at a 45° angle of incidence. There is no coating on the back side 85.

For systems in which it is desired to generate a 1.320 micron output with a Nd:YAG, a third turning mirror would be implemented that is highly reflective at 1.320 micron and transmissive at 1.064 micron. For such system, it may be necessary or desirable to align the turning mirror mechanism at a smaller angle of incidence as referred to above. This allows greater latitude in optics design with a trade-off in the efficiency of the laser system layout.

Figure 14:
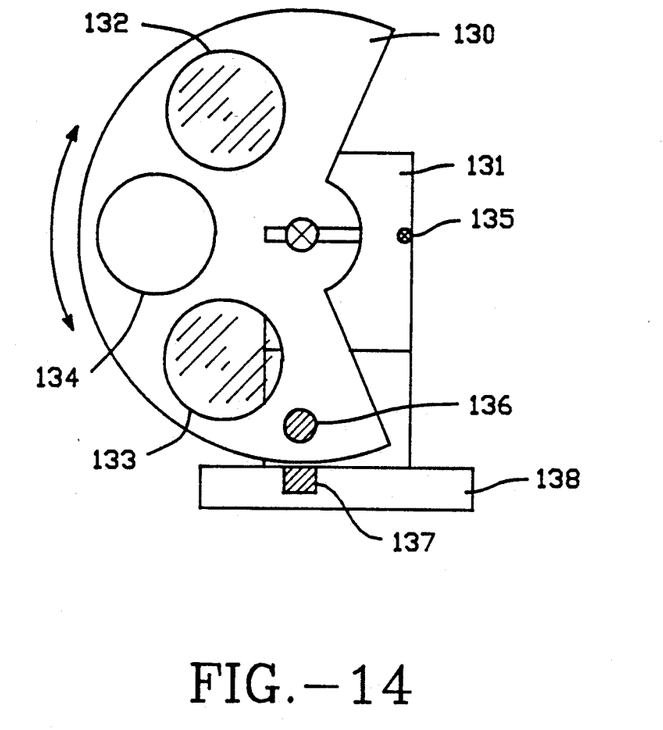
FIG. 14 illustrates the mechanism for positioning the turning mirrors in the preferred embodiment.

FIG. 14 illustrates the preferred embodiment of the turning mirror positioning mechanism. The preferred turning mirror mechanism is composed of a wheel 130 mounted on a tight shaft motor 131. The tight shaft motor in the preferred system is an Escap DC motor, model number 23L2R21213E1. The Escap DC motor 131 is a very tight shaft that minimizes vibration of the turning mirror mechanism, and maintains tight alignment for these applications. The wheel 130 has three positions corresponding to three modes of operation of a laser system. Mounted in the wheel is the first optic which is a turning mirror manufactured as illustrated in FIGS. 13A and 13B and coated for the 1.44 micron line. A second optic 133 is mounted in the wheel and coated for the 1.064 line. In between the first and second optics 132, 133, a passage 134 is provided in the wheel 130, which allows for operation in the alternate resonator mode.

The three positions are selected by operating the DC motor in a first mode in which the wheel 130 is driven against stop 135 in a clockwise direction. This position is the optic 133 in the optical path for generation of the 1.06 micron line. In the second mode, the motor is driven to approximately a center position and a magnet 136 mounted on the wheel 130 is engaged with an opposite pole magnet 137 on the base 138 of the turning mirror mechanism. The magnetic interaction holds the turning wheel 130 in position. In the third mode, the wheel 130 is driven against stop 135 in a counterclockwise direction which positions the optic 132 in the optical path for generation of the 1.44 micron line. An alternative for the magnet could be a spring mechanism.

FIG. 15 illustrates the external beam line components for the surgical laser system according to a preferred embodiment of the present invention. These beam line components are mounted on the plate 90 on which the resonator is mounted as illustrated in FIG. 9 to provide a fixed relationship between the beam delivery system and the output couplers. The output beam at 1.06 or 1.44 micron along path 105 enters the external beam path components through first turning and beam splitting prism 200. The beam path then proceeds through a collimating lens 201 into a 180° folding prism 202. Beam path then proceeds along line 203 past an exposure shutter 204, a calibration shutter 205, a safety shutter 206 and into a second turning and beam splitting prism 207. From the second turning prism 207, the beam strikes a turning mirror 208 into a coupler select mirror pair 209 and onto an endostat coupler 210 or a microbeam coupler 211 as required. The endostat coupler 210 and microbeam coupler 211 include respective fiberoptics 212, 221. The fiber 221 at the microbeam coupler 211 can only receive the laser output at 0.532 micron, While the fiber 212 at the endostat port can receive the laser output at 0.532 micron, 1.064 micron and 1.44 micron. For the 1.44 micron output, a special quartz fiber with very low water content is required to reduce the absorption at 1.44 micron to an acceptable low limit. Normal quartz fiber with higher water content can be used for 0.532 micron and 1.064 micron.

At each of the first turning prism 200 and the second turning prism 207, the beam is split and a sample of the beam is coupled to a surgical detector 213 at the first turning prism 200, or a safety detector 214 at the second turning prism 207. These detectors detect the amplitude of the beam at both the 1.064 micron and 1.440 micron lines.

The output beam along path 104 for the frequency-doubled output enters the external beam line components at dispersion prism 150. From the dispersion prism 150, it strikes a 532 nanometer turning mirror 151. The dispersion prism serves to separate the leaking 1.064 micron line which is reflected by the turning mirror 51 into a beam block 152. The 532 micron line proceeds along path 153 through a collimating lens 154 and through a surgical attenuator 155 which consist of a rotatable half-wave plate. From the surgical attenuator 155, which is coupled with polarizer pair 156, the beam passes along beam line 157 through surgical detector 158, and through the line including the exposure shutter 204, calibration shutter 205, aim detector 159, and a safety shutter 160. From the safety shutter 160, the beam proceeds through safety detector 16 and into the coupler select mirror pair 209.

For the output beams generated along line 105 which are not visible, an aim beam is provided by a helium-neon laser 150 providing an output at 0.633 micron. The output of the helium-neon laser 180 is supplied through a light valve 181 along path 182. Path 182 passes the safety shutter 206, through collimating lens 183, and through the back of turning mirror 208 and underneath the coupler select mirror pair 209. Note that the mirror pair 209 can be rotated in and out of the laser beamlines. When the mirror pair 209 is rotated out of the beamlines, the 0.532 micron output from the laser can only enter the microbeam coupler 211 and when the laser is switched to 1.064 or 1.44 micron, these outputs can only go to the endostat coupler 210. When the mirror pair 209 is rotated into the beamlines, the 0.532 micron output from the laser is directed into the endostat coupler 210. Under these conditions, the laser is not allowed to switch to 1.064 or 1.44 micron.

The components in this external beam line for the surgical system are operated under computer control to achieve output beam characteristics as desired for surgical applications, as described in our commonly owned, co-pending U.S. patent application entitled FREQUENCY DOUBLED SOLID STATE LASER HAVING PROGRAMMABLE PUMP POWER MODES AND METHOD FOR CONTROLLING LASERS, which is incorporated by reference above.

Accordingly, the present invention provides a laser system which is adaptable for a wide variety of surgical applications by means of relatively inexpensive modification of a laser resonator. Furthermore, it is capable of providing outputs at both the high gain 1.064 micron line and the low gain 1.44 micron line of Nd:YAG, which has particular importance in surgical applications.

The laser system of the present invention provides a unique surgical tool. The 1.06 micron line can be used for coagulation or tissue welding, the 1.44 micron line can be used for cutting or warming tissue based on absorption of the 1.44 micron line by water in the tissue, and the 0.532 micron line can be used for cutting in vascular tissue based on absorption by blood, and in avascular tissue based on a carbonizing reaction mechanism. Similarly, the laser system can be adapted to provide the 1.32 micron line as well, which is suitable for tissue welding or cutting. Therefore, it can be seen that the surgeon has a powerful tool in which he can adapt the wavelength provided by the laser system to the needs of the particular surgical procedure being performed. The surgeon can perform cutting using a variety of cutting mechanisms (i.e., based on absorption by water or blood) in the same procedure, he can change wavelengths using the same laser system to a coagulating or tissue welding mode with the 1.06 or 1.32 micron lines. Similarly, the 1.44 micron line is particularly suited for warming tissue at lower power based on absorption by water in the tissue. If a given line works better for a given result in certain tissues, the surgeon can make choices as necessary to optimize the results of the surgical procedure.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A laser system, comprising:
   a high reflector highly reflective at a plurality of wavelengths, and an output coupler mounted in a fixed position that is adjustable to receive the plurality of wavelengths in a resonant path;
   a gain medium, mounted in the resonant path, providing laser gain at the plurality of wavelengths;
   means for inducing laser gain to produce the gain medium in the plurality of wavelengths;
   means for selectively suppressing laser oscillation of selected subsets of the plurality of wavelengths to enable oscillation at least selected wavelengths, said means include including a plurality of non-absorbing wavelength-selective elements, and means for selectively positioning one of the plurality of said non-absorbing wavelength-selective elements in the resonant path between the high reflector and the output coupler to enable oscillation at said selected wavelengths and to generate an output beam at said selected wavelengths through said output coupler; and
   a beam delivery system, including a beam input coupler to supply the output beam from said fixed adjustable output coupler into an optical fiber, the beam delivery system mounted in a fixed position and aligned with the fixed, adjustable output coupler for efficient coupling of the output beam through the beam input coupler.

2. The laser system of claim 1, wherein the gain medium comprises Nd:YAG, and the plurality of wavelengths includes at least wavelengths near 1.06 and near 1.44 micron, and at lest one of the wavelength-selective elements suppresses oscillation at near 1.06 micron and allows oscillation at near 1.44 micron.

3. The laser system of claim 2, wherein at least another of the wavelength-selective elements allows oscillation at near 1.06 micron.

4. The laser system of claim 1, wherein the gain medium comprises Nd:YAG, and the plurality of wavelengths includes at least wavelengths near 1.32 and near 1.44 micron, and at least one of the wavelength-selective elements suppresses oscillation at near 1.32 micron and allows oscillation at near 1.44 micron.

5. The laser system of claim 4, wherein at least another of the wavelength-selective elements allows oscillation at near 1.32 micron.

6. The laser system of claim 1, wherein the gain medium comprises Nd:YAG, and the plurality of wavelengths includes at least wavelengths near 1.06, near 1.32 and near 1.44 micron, and at least one of the wavelength-selective elements suppresses oscillation at near 1.06 and near 1.32 micron, and allows oscillation near 1.44 micron.

7. The laser system of claim 6, wherein at least another of the wavelength-selective elements suppresses oscillation at near 1.06 micron and allows oscillation near 1.32 micron.

8. The laser system of claim 6, wherein at least another of the wavelength-selective elements allows oscillation at near 1.06 micron.

9. The laser system of claim 1, wherein the gain medium comprises a material providing gain at characteristic wavelengths, and the plurality of wavelengths includes at least of subset of the characteristic wavelengths.

10. The laser system of claim 1 wherein the gain medium comprises Nd:YAG providing gain at characteristic wavelengths, and the plurality of wavelengths includes at least a subset of the characteristic wavelengths.

11. The laser system of claim 1, wherein the high reflector comprises a single reflector highly reflective at the plurality of wavelengths, and the output coupler comprises a reflector greater than 75% reflective at the plurality of wavelengths.

12. The laser system of claim 1, wherein the wavelength-selective elements are essentially polarization insensitive.

13. A laser system, comprising:
   first means for highly reflecting a plurality of wavelengths along an optical path;
   fixed, adjustable output coupler for the plurality of wavelengths;
   a gain medium, mounted in the optical path, providing laser gain at the plurality of wavelengths;
   means for inducing laser gain in the gain medium in the plurality of wavelengths and generating an output beam at selected wavelengths through the output coupler;
   a plurality of beam-turning mirrors, each suppressing oscillation of at least a selected subset of the plurality of wavelengths and reflective of at least a selected wavelength, and means for selectively positioning one of the plurality of the beam-turning mirrors in the optical path, so that the output coupler and first means from a laser resonator to enable oscillation at the selected wavelength;
   a beam delivery system, including a beam input coupler to supply the output beam from said fixed, adjustable output coupler into an optical fiber, the beam delivery system mounted in a fixed position and aligned with the fixed, adjustable output coupler for efficient coupling of the output beam though the beam input coupler.

14. The laser system of claim 13, wherein the gain medium comprises Nd:YAG, and the plurality of wavelengths includes at least wavelengths near 1.06 and near 1.44 micron, and at least one of the beam-turning mirrors is transmissive at near 1.06 micron and reflective at near 1.44 micron.

15. The laser system of claim 14, wherein at least another of the beam-turning mirrors is reflective at near 1.06 micron.

16. The laser system of claim 13, wherein the gain medium comprises Nd:YAG, and the plurality of wavelengths includes at least wavelengths near 1.32 and near 1.44 micron, and at least one of the beam-turning mirrors is transmissive at near 1.32 micron and reflective at near 1.44 micron.

17. The laser system of claim 16, wherein at least another of the beam-turning mirrors is reflective at near 1.32 micron.

18. The laser system of claim 13, wherein the gain medium comprises Nd:YAG, and the plurality of wavelengths includes at least wavelengths near 1.06, near 1.32 and near 1.44 micron, and at least one of the beam-turning mirrors is transmissive at near 1.06 and near 1.32 micron and reflective at near 1.44 micron.

19. The laser system of claim 18, wherein at least another of the beam-turning mirrors is transmissive at near 1.06 micron and reflective at near 1.32 micron.

20. The laser system of claim 18, wherein at least another of the beam-turning mirrors is transmissive at near 1.32 micron and reflective at near 1.06 micron.

21. The laser system of claim 13, wherein the gain medium comprises a material providing gain at characteristic wavelengths, and the plurality of wavelengths includes at least of subset of the characteristic wavelengths.

22. The laser system of claim 13, wherein the gain medium comprises Nd:YAG providing gain at characteristic wavelengths, and the plurality of wavelengths includes at least of subset of the characteristic wavelengths.

23. The laser system of claim 13, wherein the means for positioning selectively positions the plurality of beam-turning mirrors in the optical path at an angle of incidence of near 45%.

24. The laser system of claim 13, further including an alternative resonator component mounted with in the optical path, and wherein the means for positioning positions a beam-turning mirror in the optical path so that the output coupler and first means form a laser resonator generating an output beam at the selected wavelength, or positions no beam-turning mirror in the optical path so that the alternative resonator component and the first means form an alternative laser resonator.

25. A laser system, comprising:
first means for highly reflecting a plurality of wavelengths along an optical path;
a fixed, adjustable output coupler for the plurality of wavelengths to provide a first output beam;
a gain medium, mounted in the optical path, providing laser gain at the plurality of wavelengths;
means for inducing laser gain in the gain medium in the plurality of wavelengths and generating an output beam at selected wavelengths through the fixed, adjustable output coupler;
means, mounted in the optical path, for extracting an output wavelength derived from one of the plurality of wavelengths, said means further including means for directing a reflected beam along the optical path to form a laser resonator with the first means and provide a second output beam; a plurality of wavelength-selective beam-turning elements, and means for positioning a selected one of the wavelength-selective beam-turning elements in the optical path for directing a selected wavelength of the plurality of wavelengths toward the fixed, adjustable output coupler so that the fixed, adjustable output coupler and first means form a laser resonator generating the output beam at a selected wavelength, or positioning none of the wavelength-selective beam-turning elements in the optical path to direct at least one wavelength toward the means for extracting sot hat the means for extracting and the first means form a laser resonator generating the second output beam; and
a beam delivery system, including a beam input coupler to supply the first output beam into an optical fiber, the beam delivery system mounted in a fixed position and aligned with the fixed, adjustable output coupler for efficient coupling of the first output beam though the beam input coupler.

26. The laser system of claim 25, wherein the wavelength derived from the one wavelength is a second harmonic of the one wavelength.

27. The laser system of claim 25, wherein the gain medium comprises Nd:YAG, and the plurality of wavelengths includes at least wavelengths near 1.06 and near 1.44 micron, and the beam-turning means includes at lest one beam-turning element transmissive at near 1.06 micron and reflective at near 1.44 micron.

28. The laser system of claim 27, wherein the beam-turning means includes at least another beam-turning element reflective at near 1.06 micron.

29. The laser system of claim 27, wherein the wavelength derived from the one wavelength is a second harmonic of the wavelength near 1.06 micron.

30. The laser system of claim 25, wherein the gain medium comprises Nd:YAG, and the plurality of wavelengths includes at least wavelengths near 1.32 and near 1.44 micron, and beam-turning means includes at least one beam-turning element transmissive at near 1.32 micron and reflective at near 1.44 micron.

31. The laser system of claim 30, wherein beam-turning means includes at least another beam-turning element reflective at near 1.32 micron.

32. The laser system of claim 30, wherein the wavelength derived from the one wavelength is a second harmonic of the wavelength near 1.32 micron.

33. The laser system of claim 25, wherein beam-turning elements in the beam-turning means include a plurality of turning mirrors; and a means, coupled to the plurality of beam-turning mirrors, for selectively positioning the plurality of beam-turning mirrors in the optical path.

34. The laser system of claim 33, herein the means for positioning positions a selected beam-turning mirror in the optical path at an angle of incidence of near 45%.

35. The laser system of claim 25, wherein the gain medium comprises a material providing gain at characteristic wavelengths, and the plurality of wavelengths includes at least of subset of the characteristic wavelengths.

36. The laser system of claim 25, wherein the gain medium comprises Nd:YAG providing gain at characteristic wavelengths, and the plurality of wavelengths includes at least of subset of the characteristic wavelengths.

37. A laser system, comprising:
a high reflector, a beam-turning mirror and a fixed, adjustable output coupler in a resonant path for outputting a wavelength near 1.44 micron;
an Nd:YAG gain medium, mounted in the resonant path, for providing laser gain; and
means for including laser gain in the gain medium to generate an output beam through the fixed, adjustable output coupler; wherein
the beam-turning mirror is reflective at near 1.44 micron and transmissive at least one higher gain line of the Nd:YAG gain medium, while suppressing oscillation at higher gain lines and enabling oscillation at near 1.44 micron; and
a beam delivery system, including a beam input coupler to supply the output beam into an optical fiber, the beam delivery system mounted in a fixed positions and aligned with the fixed, adjustable output coupler for efficient coupling of the output beam though the beam input coupler.

38. A laser system, comprising:
a gain medium for providing laser gain at a plurality of wavelengths;
means, coupled with the gain medium, for inducing laser gain int eh gain medium in the plurality of wavelengths;
a first fixed, adjustable output coupler having a first selected wavelength to supply a first output beam;
a second fixed, adjustable output coupler having a second selected wavelength to supply a second output beam;
means, supporting the gain medium, for selectively aligning the gain medium with one of the first or the second fixed, adjustable output coupler to selectively enable laser oscillation of selected wavelengths along an optical path through the gain medium; and
beam delivery means, mounted in fixed relationship to the first and second fixed, adjustable output couplers, for receiving the first and second output beams from the first and second fixed, adjustable output couplers and selectively delivering one of the first and second output beams to a work site.

* * * * *